United States Patent

Park et al.

[11] Patent Number: 5,882,687
[45] Date of Patent: Mar. 16, 1999

[54] COMPOSITIONS AND METHODS FOR STORING CONTACT LENSES

[75] Inventors: John Y. Park, Tustin; Daniel Cafaro, Walnut Creek; Anthony J. Dziabo, Lake Forest, all of Calif.

[73] Assignee: Allergan, Waco, Tex.

[21] Appl. No.: 781,869

[22] Filed: Jan. 10, 1997

[51] Int. Cl.⁶ .................................................... A61K 30/16
[52] U.S. Cl. ................ 424/682; 252/106; 514/6
[58] Field of Search ............................ 252/106; 424/682; 514/6

[56] References Cited

U.S. PATENT DOCUMENTS

| | | |
|---|---|---|
| 3,150,045 | 9/1964 | Boghosian . |
| 4,039,662 | 8/1977 | Hecht et al. . |
| 4,409,205 | 10/1983 | Shively . |
| 4,560,491 | 12/1985 | Sherman . |
| 4,819,617 | 4/1989 | Goldberg et al. . |
| 5,002,582 | 3/1991 | Guire et al. ............................ 623/66 |
| 5,075,104 | 12/1991 | Gressel et al. . |
| 5,141,665 | 8/1992 | Sherman . |
| 5,353,445 | 10/1994 | Lavaux . |
| 5,460,834 | 10/1995 | Bhagat . |
| 5,461,081 | 10/1995 | Ali et al. . |
| 5,494,155 | 2/1996 | Evans et al. . |

FOREIGN PATENT DOCUMENTS

| | | |
|---|---|---|
| 8494681 | 12/1984 | WIPO . |
| 9304706 | 3/1993 | WIPO . |

*Primary Examiner*—Keith D. MacMillan
*Attorney, Agent, or Firm*—Carlos A. Fisher, Esq.; Timothy J. King, Esq.

[57] ABSTRACT

Compositions for storing contact lenses include a liquid medium containing a polyanionic component, preferably a water soluble polyanionic component, in an amount effective to provide a hydration layer on the surface of said contact lens. The composition has a viscosity of less than 50 cps at 25° C., an osmolality of at least about 200 mOsm/kg, and preferably a pH in the range of about 6 to about 9.

16 Claims, No Drawings

COMPOSITIONS AND METHODS FOR STORING CONTACT LENSES

BACKGROUND OF THE INVENTION

This invention relates to compositions and methods useful in contact lenses. More particularly, the invention relates to compositions and methods in which contact lenses are stored. The present invention provides compositions containing polyanionic components.

The current commercial process for packaging contact lenses is to place a single contact lens in a glass vial, fill the vial with saline solution, cap and seal the vial and then heat sterilize of the lens. This process is also used for daily-disposable lenses. Indeed, this packaging process results in one of the meritorious attributes with the use of daily-disposable lenses: comfort associated with wearing fresh lenses every day. However, symptoms of discomfort, fatigue, and irritation at the end of the day are common among daily-disposable lens wearers. To alleviate or reduce the aforementioned symptoms, incorporation of a comfort enhancing agent(s) and/or a lubricant(s) into the lens storage medium is highly desirable, which also can make the extension of the lens wearing time possible. This is critical to the consumer of a daily-disposable lens.

Since the current packaging process requires heat sterilization, commonly used lubricants like polyvinyl alcohol (PVA), polyethylene glycol (PEG), hydroxypropyl methylcellulose (HPMC) are not suitable for this purpose due to their physio-chemical instabilities. A suitable lubricant should have a high affinity toward water and contact lens surface so that a hydration layer can be formed on the lens surface. For example, upon heating, HPMC in aqueous solution loses water from the hydration. As a result, it loses lubricity on the lens surface.

Bhagat, U.S. Pat. No. 5,460,834 discloses the use of cellulose polymers for use in physiological tear compositions. However, this patent does not disclose use of such cellulose polymers for providing a lubricant in conjunction with a contact lens storage medium.

It would be advantageous to provide a new contact lens storage system for daily-disposable contact lenses.

SUMMARY OF THE INVENTION

New compositions, and methods for use thereof, which include polyanionic components have been discovered. Thus, in accordance with the present invention, polyanionic components are utilized in solutions in which contact lenses are packaged prior to dispensing.

It has been surprisingly discovered that carboxymethylcellulose (CMC), a polyanionic polymer, which forms a hydration layer on the surface of the contact lens which provides a unique and effective lubricity for all contact lenses, can be heat-sterilized safely together with a contact lens without eliminating its lubricating effects. Thus, it is an ideal lubricant for the medium in which contact lenses are packaged.

CMC in aqueous solution, unlike HPMC, does not lose water upon heating and forms a hydration layer on the lens surface, but does not lower surface tension of the aqueous solution. Additionally, CMC has a strong binding affinity toward proteins-lysozymes. Thereby, it prevents and/or delays protein deposits from forming on the lens surface. Thus, it provides additional benefits to lens wearers.

The present compositions are straightforward, easy and inexpensive to produce and use and provide outstanding benefits. Because the components are preferably water soluble, they can be utilized in very easy to practice methods for lubricating daily-disposable contact lenses. A storage medium containing a polyanionic component is envisioned. The present invention improves the lubricity of contact lenses upon removal from the glass or plastic container in which they are disposed. Such lenses are presently packaged in isotonic saline solution.

In one broad aspect of the present invention, compositions comprising a liquid medium and a polyanionic component are provided. The polyanionic component is included in the liquid medium in an amount, preferably of at least 0.01% by weight per volume (w/v) of the composition, effective to form a hydration layer at the surface of the contact lens. The composition preferably has a viscosity of less than 50 cps at 25° C. and an osmolality of at least about 200 mOsm/kg. More preferably, the composition has a pH in the range of about 6 to about 8 or about 9 so that the composition is ophthalmically acceptable.

A material is "ophthalmically acceptable" if the material can be placed in or on a mammalian eye, preferably human, without causing any significant damage or harm to the eye.

The polyanionic component and any precursor thereof preferably do not act as a delayed release component, that is, it does not act to substantially (for a controlled or substantially predetermined period of time) delay the release of another component in the composition and any liquid-containing precursor thereof. In other words, the present polyanionic components are effective to provide lubrication and preferably are not employed, in the present invention, as delayed release components.

The liquid medium preferably comprises water, and the polyanionic component is preferably water soluble.

As used herein, the term "polyanionic component" refers to a chemical entity, for example, an ionically charged species, such as an ionically charged polymeric material, which includes more than one discrete anionic charge, that is, the chemical entity has more than one discrete anionic charge. Preferably, the polyanionic component is selected from the group consisting of polymeric materials having multiple anionic charges and mixtures thereof. Particularly useful anionic components are selected from anionic cellulose derivatives, anionic polymers derived from acrylic acid (meaning to include polymers from acrylic acid, acrylates and the like and mixtures thereof), anionic polymers derived from methacrylic acid (meaning to include polymers from methacrylic acid, methacrylates, and the like and mixtures thereof), anionic polymers derived from alginic acid (meaning to include alginic acid, alginates, and the like and mixtures thereof), anionic polymers of amino acids (meaning to include polymers of amino acids, amino acid salts, and the like and mixtures thereof), and the like and mixtures thereof. Useful polyanionic components are those selected from anionic cellulose derivatives and mixtures thereof, especially carboxymethylcelluloses. Carboxymethylcelluloses include the salts of carboxymethylcellulose. Preferably, the polyanionic compound is carboxymethylcellulose sodium.

Methods for storing contact lenses are included within the scope of the present invention. These methods comprise immersing a contact lens in a liquid medium containing a polyanionic component as described herein.

In addition, one or more other components can be added to the presently useful compositions to provide one or more further benefits and/or improvements to the contact lens being treated and/or to the wearer of the treated lens.

These and other aspects of the present invention will become apparent hereinafter, particularly when considered in conjunction with the following detailed description, examples and claims.

DETAILED DESCRIPTION OF THE INVENTION

The present compositions are applicable for use with all types of contact lenses. Preferably, the present compositions are packaged with daily-disposable lenses. These contact lenses may be made of any material or combination of materials and may have any suitable configuration.

Any suitable polyanionic component may be employed in accordance with the present invention provided that it functions as described herein and has no substantial detrimental effect on the contact lens being stored or on the wearer of the contact lens. The polyanionic component is preferably ophthalmically acceptable at the concentrations used. The polyanionic component preferably includes three (3) or more anionic (or negative) charges. In the event that the polyanionic component is a polymeric material, it is preferred that each of the repeating units of the polymeric material include a discrete anionic charge. Particularly useful anionic components are those which are water soluble, for example, soluble at the concentrations used in the presently useful liquid aqueous media, such as a liquid aqueous medium containing the polyanionic component. Particularly useful polyanionic compounds are those which are not eliminated during terminal sterilization of packaged contact lenses.

A particularly useful class of polyanionic components are one or more polymeric materials having multiple anionic charges. Examples include:

metal carboxymethylcelluloses
metal carboxymethylhydroxyethylcelluloses
metal carboxymethylstarchs
metal carboxymethylhydroxyethylstarchs
hydrolyzed polyacrylamides and polyacrylonitriles heparin
homopolymers and copolymers of one or more of:
  acrylic and methacrylic acids
  metal acrylates and methacrylates
  alginic acid
  metal alginates
  vinylsulfonic acid
  metal vinylsulfonate
  amino acids, such as aspartic acid, glutamic acid and the like
  metal salts of amino acids
  p-styrenesulfonic acid
  metal p-styrenesulfonate
  2-methacryloyloxyethylsulfonic acids
  metal 2-methacryloyloxethylsulfonates
  3-methacryloyloxy-2-hydroxypropylsulfonic acids
  metal 3-methacryloyloxy-2-hydroxypropylsulfonates
  2-acrylamido-2-methylpropanesulfonic acids
  metal 2-acrylamido-2-methylpropanesulfonates
  allylsulfonic acid
  metal allylsulfonate and the like.

The present polyanionic components often can exist in the un-ionized state, for example, in the solid state, in combination with a companion or counter ion, in particular a plurality of discrete cations equal in number to the number of discrete anionic charges so that the un-ionized polyanionic component is electrically neutral. For example, the present un-ionized polyanionic components may be present in the acid form and/or in combination with one or more metals. Since the polyanionic components are preferably ophthalmically acceptable, it is preferred that the metal associated with the un-ionized polyanionic component be ophthalmically acceptable in the concentrations used. Particularly useful metals include the alkali metals, the alkaline earth metals, for example, calcium and magnesium, and mixtures thereof. Sodium is very useful to provide the counter ion in the un-ionized polyanionic component. Polyanionic components which, in the un-ionized states, are combined with cations other than H+ and metal cations can be employed in the present invention.

Particularly useful polyanionic components are selected from anionic cellulose derivatives, anionic polymers derived from acrylic acid (meaning to include polymers from acrylic acid, acrylates and the like and mixtures thereof), anionic polymers derived from methacrylic acid (meaning to include polymers from methacrylic acid, methacrylates, and the like and mixtures thereof), anionic polymers derived from alginic acid (meaning to include alginic acid, alginates, and the like and mixtures thereof), anionic polymers derived from amino acids (meaning to include amino acids, amino acid salts, and the like and mixtures thereof) and mixtures thereof. Very useful polyanionic components are those selected from anionic cellulose derivatives and mixtures thereof, especially carboxymethylcelluloses.

The amount of polyanionic component employed is that amount effective to function as described herein. Preferably the polyanionic component is present in the composition of the invention in an amount of at least 0.01% w/v. The specific amount of such component used is not critical to the present invention provided that it functions as described herein. In addition, the amount of polyanionic components employed depends on a number of factors, for example, the specific polyanionic component being employed. In addition, excessive amounts of polyanionic component are preferably to be avoided since this may be wasteful and unnecessary and may have an adverse impact on the wearer of the disinfected contact lens. Preferably, the polyanionic component is present in an amount of at least about 0.01% w/v or at least about 0.05% w/v to about 5% w/v or about 2% w/v or about 1% w/v.

Many of the materials useful as polyanionic components in the present invention have previously been used as delayed release components. Therefore, it is important to note that the ability of a material to act to enhance lubricity is substantially different from and independent of the ability of a material to act as a delayed release component.

The liquid media useful in the present invention are selected to have no substantial detrimental effect on the lens being treated or cared for and to allow or even facilitate the present lens treatment or treatments. The liquid media are preferably aqueous-based. A particularly useful aqueous liquid medium is that derived from saline, for example, a conventional saline solution or a conventional buffered saline solution. During the composition-contact lens contacting step or steps, for example, during contact lens packaging, the aqueous liquid medium preferably has a pH in the range of about 6 to about 9 or about 10, more preferably about 6 to about 8, and still more preferably about 7.5. The liquid medium preferably has a ophthalmically acceptable tonicity level, for example, of at least about 200 mOsm/kg, more preferably in the range of about 200 to about 400 mOsm/kg.

The liquid media containing the polyanionic components preferably have viscosities of less than 50 centipoise (cps) at 25° C., and more preferably less than about 25 cps or about 20 cps at 25° C.

In order to ensure that the pH of the aqueous liquid medium is maintained within the desired range, the aqueous liquid medium may include at least one buffer component. Although any suitable buffer component may be employed, it is preferred to select such component so as not to substantially detrimentally affect the polyanionic component. It is preferred that the buffer component be inorganic. Alkali metal and alkaline earth metal buffer components are advantageously used in the present invention.

Further, in order to avoid possible eye irritation, it is preferred that the presently useful liquid media have an osmolality (a measure of tonicity) of at least about 200 mOsm/kg, preferably in the range of about 200 to about 350 or about 400 mOsm/kg. In an especially useful embodiment, the osmolality or tonicity of the liquid medium substantially corresponds to the tonicity of the fluids of the eye, in particular the human eye.

Any suitable ophthalmically acceptable tonicity component or components may be employed, provided that such component or components are compatible with the other ingredients of the precursor liquid medium and do not have deleterious or toxic properties which could harm the eye. Examples of useful tonicity components include sodium chloride, potassium chloride, mannitol, dextrose, glycerin, propylene glycol and mixtures thereof. In one embodiment, the tonicity component is selected from inorganic salts and mixtures thereof.

The amount of ophthalmically acceptable tonicity component utilized can vary widely. In one embodiment, the tonicity component is preferably present in the liquid medium in an amount in the range of about 0.5 to about 0.9 weight/volume percent of the formulation.

Typical of ophthalmically acceptable inorganic salt tonicity components are alkali metal chlorides and alkaline earth metal chlorides, such as sodium chloride, potassium chloride, calcium chloride and magnesium chloride.

One or more additional components can be included in the presently useful liquid media. Such additional component or components are chosen to impart or provide at least one beneficial or desired property to the liquid media. Such additional components may be selected from components which are conventionally used in one or more contact lens care compositions. Examples of such additional components include cleaning agents, wetting agents, nutrient agents, sequestering agents, viscosity builders, contact lens conditioning agents, antioxidants, and the like. These additional components may each be included in the liquid medium in an amount effective to impart or provide the beneficial or desired property to the liquid medium. For example, such additional components may be included in the presently useful liquid media in amounts similar to the amounts of such components used in other, e.g., conventional, contact lens care products.

Examples of useful sequestering agents include disodium ethylene diamine tetraacetate, alkali metal hexametaphosphate, citric acid, sodium citrate and mixtures thereof.

Examples of useful viscosity builders include hydroxyethyl cellulose, hydroxymethyl cellulose, polyvinyl pyrrolidone, polyvinyl alcohol and mixtures thereof.

Examples of useful antioxidants include sodium metabisulfite, sodium thiosulfate, N-acetylcysteine, butylated hydroxyanisole, butylated hydroxytoluene and mixtures thereof.

The following non-limiting examples illustrate certain aspects of the present invention.

EXAMPLE 1

A solution is prepared by blending the various components together and has the following composition:

| | |
|---|---|
| Sodium carboxymethyl cellulose (USP) | 0.2% (w/v) |
| Sodium chloride (USP) | 0.75% (w/v |
| Hydrochloric acid or sodium hydroxide | pH adjusted to 7.4 |
| Boric acid (NF) | 0.15% (w/v) |
| Purified water (USP) | Q.S. to volume |

When it is desired to package a contact lens, it is placed in a conventional lens container suitable for storing the lens. Glass containers are preferable when the contact lenses and their storage solution are to be heat sterilized. However, Wöhlk of Schönkirchen, Germany packages contact lenses for dispensing in a plastic container which can survive heat sterilization. Plastic containers are preferable when the contact lenses and their storage solutions are sterilized by gamma radiation. Preferably a 10 ml quantity of the solution is placed in the lens container. However, less solution may be used. The package is sealed and is either heat treated or treated with gamma radiation. Upon removal from the package, the lens may be placed directly in the human eye.

Thus, contact lens storage media formulations including effective contact lens lubricating amounts of synthetic or natural water soluble polyanionic components, such as polymers of this type, can be used to effectively lubricate the contact lens so the lenses are comfortable to the wearer upon insertion into the eye. This storage media is particularly beneficial for daily-disposable lenses.

EXAMPLE 2

A solution is prepared by blending the various components together and has the following composition:

| | |
|---|---|
| Sodium carboxymethylcellulose (USP) | 0.5% (w/v) |
| Sodium chloride (USP) | 0.62% (w/v) |
| Boric acid | 0.2% (w/v) |
| Potassium chloride (USP) | 0.14% (w/v) |
| Calcium chloride dihydrate (USP) | 0.02% (w/v) |
| Magnesium chloride hexahydrate (USP) | 0.006% (w/v) |
| Sodium hydroxide (NF) | adjust to pH 7.6 |
| Purified Water | Q.S. to volume |

This solution is to be used in the same manner as provided in Example 1.

EXAMPLE 3

Example 2 is repeated except that the solution additionally includes 0.00085% w/v of vitamin B-12.

Substantially the same results are obtained using this solution as are obtained using the solution of Example 2. In addition, the solution of this Example 3 has a distinctive rose color.

EXAMPLE 4

A solution is prepared by blending the various components together and has the following composition:

| | |
|---|---|
| Sodium carboxymethylcellulose (USP) | 0.2% (w/v) |
| Sodium chloride (USP) | 0.75% (w/v) |
| Boric acid (NF) | 0.15% (w/v) |
| Hydrochloric acid or Sodium hydroxide | Adjust to pH 7.4 |
| Purified water (USP) | Q.S. to volume |

A quantity of this solution is placed, together with a daily-disposable contact lens, in a conventional daily-disposable contact lens package useful for transporting, storing (prior to use) and dispensing daily-disposable contact lenses. The package is then terminally sterilized either with heat or gamma radiation. The lens remains in the package until it is removed from the package and placed directly into the eye for safe and comfortable wear.

The solution is an effective, non-toxic, non-irritating and comforting (soothing and lubricating) storage medium for dispensing new soft and rigid gas permeable contact lenses, for example, daily-disposable contact lenses.

While this invention has been described with respect to various specific examples and embodiments, it is to be understood that the invention is not limited thereto and that it can be variously practiced with the scope of the following claims.

What is claimed is:

1. A contact lens storage solution comprising:

a soluble component selected from the group consisting of a carboxymethyl cellulose, a carboxymethyl starch, a carboxymethylhydroxyethyl cellulose, and a carboxymethylhydroxyethyl starch, wherein said soluble component is present in an amount effective to enhance the lubricity of a contact lens stored in said solution when said lens is placed in the human eye, said solution having a viscosity of less than 50 cps at 25° C. and an osmolality of at least 200 mOsm/kg, and said solution further being stable to heat and radiation sterilization and containing no additional disinfectant component.

2. The solution of claim 1, wherein said soluble component is in an amount of at least 0.01% w/v.

3. The solution of claim 1, wherein said soluble component is in an amount of at least 0.01% w/v but not more than 2.0% w/v.

4. The solution of claim 1, wherein said soluble component is in an amount of at least 0.1% w/v but not more than 1.0% w/v.

5. The solution of claim 1, further comprising an effective amount of a tonicity adjusting component and an effective amount of a pH buffering component, wherein said solution has a pH in the range of about 6 to about 9.

6. The solution of claim 1, which further comprises a vitamin B-12 in an amount effective to provide a distinctive color thereto.

7. The solution of claim 1, wherein said soluble component is selected from the group consisting of carboxymethylcellulose and mixtures thereof.

8. A method of preparing a package comprising a storable, sterile contact lens suitable for immediate use comprising:

immersing a contact lens in a solution comprising a soluble polyanionic component in an amount effective to enhance the lubricity a of contact lens stored in said solution when placed in the human eye, said solution having a viscosity of less than 50 cps at 25° C. and an osmolality of at least 200 mOsm/kg and a pH in the range of about 6 to about 9;

packaging the solution and the lens in a manner preventing contamination of said lens by microorganisms; and sterilizing the packaged solution and lens.

9. The method of claim 8, wherein said polyanionic component is selected from the group consisting of carboxymethylcelluloses and mixtures thereof.

10. The method of claim 6, wherein said polyanionic component is in an amount of at least 0.01% w/v but not more than 2.0% w/v.

11. The method of claim 8, wherein said polyanionic component is in an amount of at least 0.1% w/v but not more than 1.0% w/v.

12. The package of claim 8, wherein the container means is a glass vial.

13. The package of claim 8 further comprising a sealing means to prevent contamination to said solution.

14. The package of claim 8, wherein said soluble component is in an amount of at least 0.01% w/v but not more than 2.0% w/v.

15. The package of claim 8, wherein said soluble component is in an amount of at least 0.1% w/v but not more than 1.0% w/v.

16. A package containing a contact lens suitable for immediate use which comprises:

a) a solution comprising a soluble component selected from the group consisting of: a carboxymethyl cellulose, a carboxymethyl starch, a carboxymethylhydroxyethyl cellulose, and a carboxymethylhydroxyethyl starch and having a viscosity of less than 50 cps at 25° C., an osmolality of at least about 200 mOsm/kg and a pH in the range of about 6 to about 9;

b) at least one contact lens, and c) a container for holding said solution and contact lens sufficient to preserve the sterility of said solution and contact lens, wherein said solution contains no additional disinfectant component.

* * * * *